United States Patent
Lipkin et al.

(10) Patent No.: US 6,537,816 B1
(45) Date of Patent: Mar. 25, 2003

(54) STANDARDS, METHODS FOR MAKING, AND METHODS FOR USING THE STANDARDS IN EVALUATION OF OXIDE REMOVAL

(75) Inventors: Don Mark Lipkin, Niskayuna, NY (US); Paul Leonard Dupree, Scotia, NY (US); Scott Andrew Weaver, Ballston Lk., NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/332,617

(22) Filed: Jun. 14, 1999

(51) Int. Cl.[7] .............................................. G01N 31/00
(52) U.S. Cl. .................. 436/6; 436/5; 422/53; 428/544; 428/575
(58) Field of Search ........................ 436/5, 6; 422/53; 73/865.9, 866, 866.4; 428/544.1, 551, 552, 574–577, 580, 581, 586–589, 571–575, 472.1, 47.2

(56) References Cited

U.S. PATENT DOCUMENTS

| 2,617,293 | A | * | 11/1952 | Schnadt ........................ 73/844 |
| 4,285,459 | A | * | 8/1981 | Baladjanian et al. ....... 228/194 |
| 4,525,250 | A | * | 6/1985 | Fahrmbacher-Lutz et al. ... 205/212 |
| 4,842,674 | A | * | 6/1989 | Freti et al. ..................... 356/43 |
| 5,147,802 | A | * | 9/1992 | Aspden et al. .................. 436/43 |
| 5,292,481 | A | * | 3/1994 | Aspden et al. ................. 422/53 |

FOREIGN PATENT DOCUMENTS

JP          357093234 A   *   6/1982

OTHER PUBLICATIONS

Darmetal Sàrl, Metallurgical engineering: http://www.darmetal.com/page1.htm, "All kind of steel products, prepainted galvanised steel, galvanized steel, . . . ".*

* cited by examiner

Primary Examiner—Jill Warden
Assistant Examiner—Yelena Gakh
(74) Attorney, Agent, or Firm—Paul J. DiConza; Patrick K. Patnode

(57) ABSTRACT

An article of manufacture forms a tool for determining cleaning parameters of an oxide removal process. The article comprises a block of material upon which an oxide can be formed and a simulated defect structure disposed in the block of material. The article is capable of determining oxide removal parameters of an oxide removal process by disposing an oxidized standard in a reactor, conducting an oxide removal process to remove oxide from the standard, and evaluating the standard and simulated defect structure for remaining oxide and other oxide removal parameters.

6 Claims, 3 Drawing Sheets

STANDARDS, METHODS FOR MAKING, AND METHODS FOR USING THE STANDARDS IN EVALUATION OF OXIDE REMOVAL

BACKGROUND OF THE INVENTION

The invention relates to standards for evaluating oxide removal, methods of making the standards, and their associated methods of use.

Aeronautical, marine, and land-based turbine components, such as, but not limited to, blades, shrouds, and vanes, are exposed to high-temperature oxidizing, and often corrosive, environments during service. Surfaces of turbine components, including cracks, may form complex, chemically stable thermal oxides during use. These oxides comprise, but are not limited to, oxides of aluminum, titanium, chromium, and combinations thereof.

Turbine components are periodically overhauled in order to prolong life or enhance performance. During these overhauls, the turbine components may be subjected to various repair operations, including welding, brazing, or coating. The presence of stable oxides impairs the reparability of a superalloy. Therefore, removal of these oxides prior to repair, for example by cleaning the turbine components, is important for successful turbine overhaul.

Grit-blasting or grinding operations can effectively remove surface oxides when only superficial repairs are required and the surfaces to be cleaned are readily accessible. These cleaning operations, however, are not only labor intensive but can result in inadvertent and undesirable loss of the base alloy material, thus compromising the turbine component's reliability and efficiency. Further, repair of hard-to-reach surfaces, including internal passages and highly concave sections, such as, but not limited to, cooling holes, cracks, and slots, generally requires a non-mechanical cleaning process that minimally degrades or consumes the base alloy. These cleaning processes have included batch thermo-chemical cleaning, such as processes that occur in a high-temperature reactive environment. These batch turbine-component cleaning processes can, in some cases, rely on fluoride ions, which are provided in a reactor to remove highly stable oxides from cooling holes, cracks, slots, and other hard-to-reach surfaces. The fluoride-ion cleaning (FIC) processes are known to remove oxides while leaving the turbine component's base alloy essentially intact.

While processes such as FIC are useful for cleaning oxides on turbine components, the process effectiveness, especially with respect to oxide removal from cooling holes, cracks, slots, and other hard-to-reach surfaces, is difficult to quantify. Known measures of oxide removal comprise sectioning of cleaned turbine components and measuring the extent of oxide cleaning. This measure does not provide a consistent indication of overall oxide removal, since both the damage and oxidation characteristics of each turbine component will vary. Therefore, a tool that can consistently gauge the effectiveness of an oxide removal process would be desirable.

SUMMARY OF THE INVENTION

The invention sets forth an article of manufacture comprising a block of material upon which an oxide can be formed and a defect structure disposed in the block of material. The article is capable of being used to assess the effectiveness of an oxide removal process by measuring oxide removal from the block and defect structure after subjecting it to an oxide removal process.

The invention further sets forth a tool for determining oxide removal parameters of an oxide removal process. The tool comprises a block of material upon which an oxide can be formed and a defect structure disposed in the block of material. The tool is capable of being used to assess the effectiveness of an oxide removal process by measuring oxide removal from the block and defect structure after subjecting it to an oxide removal process.

Another embodiment of the invention provides a process for determining an oxide removal effectiveness. The process comprises disposing an oxidized standard in a reactor that is capable of oxide removal. The standard comprises a block of material upon which an oxide can be formed and a defect structure disposed in the block of material. The method further includes conducting an oxide cleaning and evaluating the standard for remaining oxide.

A further embodiment of the invention comprises a process for forming an oxide removal evaluation standard. The standard comprises a block of material upon which an oxide can be formed and a defect structure disposed in the block of material. The process comprises machining the slot structure in the block of material, compressing the defect structure to form at least one crack-like defect, and exposing the block of material to a thermal treatment to form an oxide on the block surfaces and within the at least one crack-like defect.

These and other aspects, advantages and salient features of the invention will become apparent from the following detailed description, which, when taken in conjunction with the annexed drawings, where like parts are designated by like reference characters throughout the drawings, disclose embodiments of the invention.

DETAILED DESCRIPTION OF THE INVENTION

Oxide removal from engine-run turbine components is an important step in turbine component repair and overhaul processes. The invention provides a tool for evaluating performance of oxide removal processes. The tool is useful in quantifying oxide removal from cracks and other hard-to-reach surfaces, including cooling holes, slots, internal passages, and other highly concave sections (hereinafter referred to as "defects").

The tool, as embodied by the invention, comprises a standard specimen that enables the extent and effectiveness of oxide removal to be evaluated. The standard comprises a solid article, for example an article having a generally rectangular-solid geometry. The standard typically comprises a material similar to that which is to be cleaned. For example, and in no way limiting of the invention, if an oxide removal process is used in repair of turbine components that are formed of superalloy materials, the standard is formed from a similar superalloy material, such as nickel-, cobalt-, or iron-based superalloys, or combinations thereof.

Figure 1:
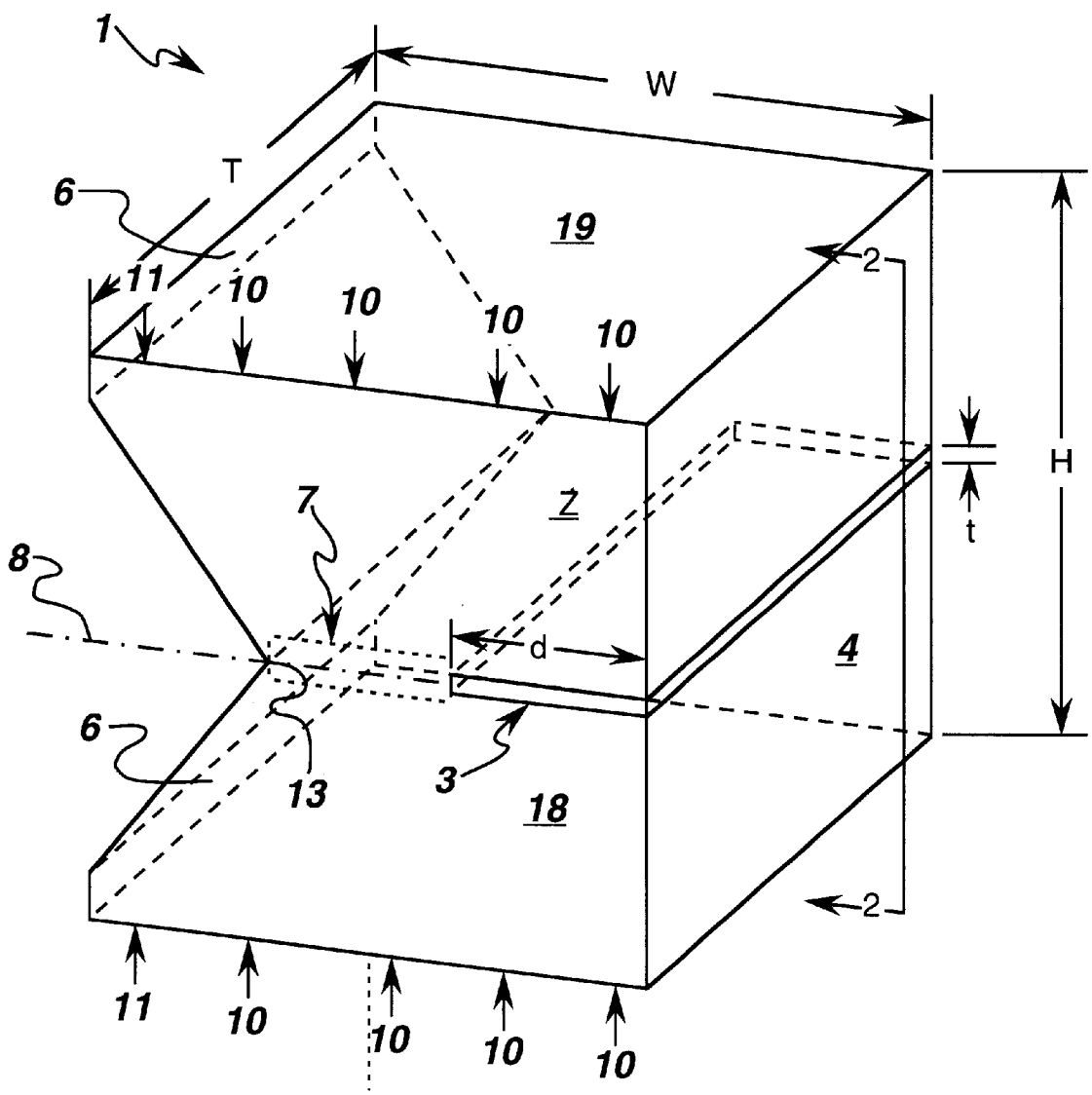
FIG. 1 is a schematic illustration of a standard for evaluating effectiveness of oxide removal processes.
Figure 2:
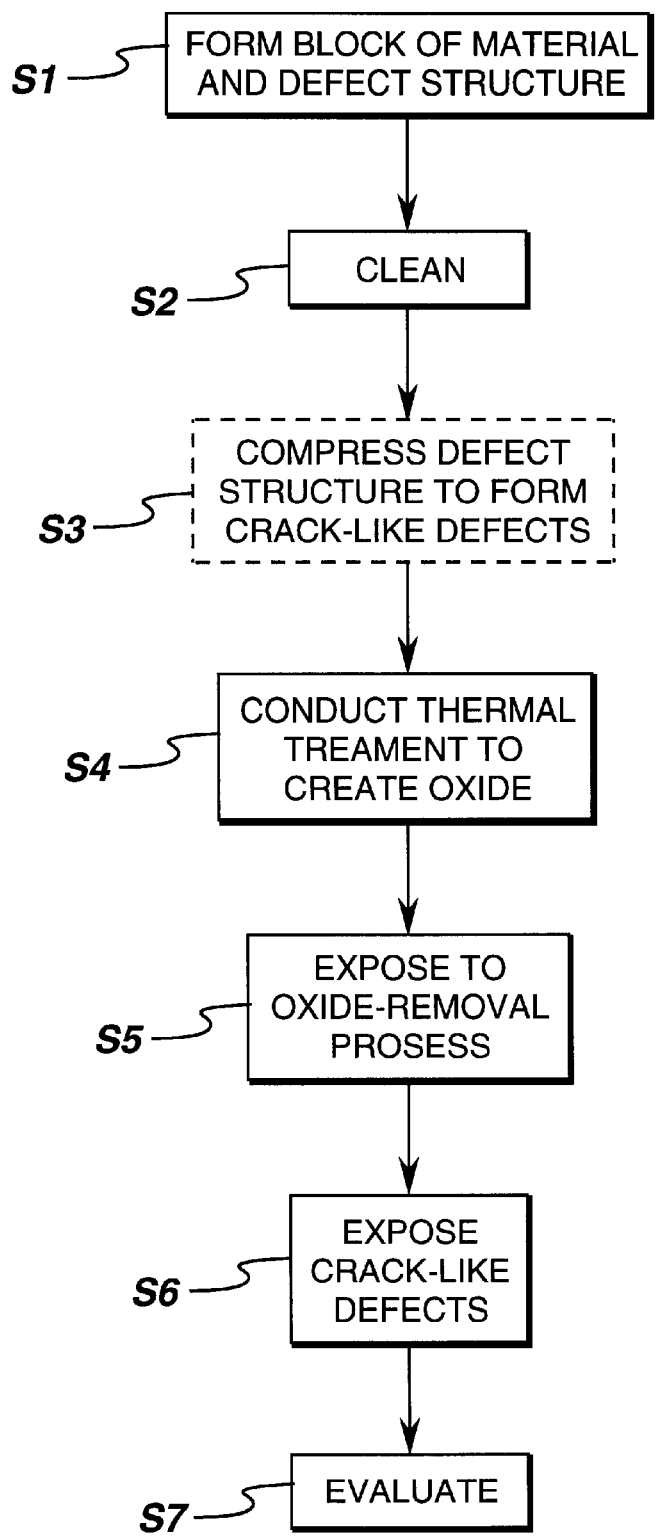
FIG. 2 is a flow chart of a method for making and using standards, as embodied by the invention, and for evaluating effectiveness of oxide removal processes.

One embodiment of a standard 1 will be described, along with methods of its formation and use, with reference to FIGS. 1 and 2 and the flowchart of FIG. 3. The following structure is merely exemplary of standards within the scope of the invention, and is not meant to limit the invention in any way. The standard 1 comprises a solid block 2 (hereinafter "block"), for example a block formed of a superalloy material. The scope of the invention includes forming the block 2 in any appropriate shape, including but not limited to, a general rectangular solid. The block 2 may also comprise protrusions and depressions formed thereon. The following description of the invention will refer to a generally rectangular block, however this is merely exemplary and is not meant to limit the invention in any way.

The block 3 includes a defect structure. The defect structure comprises at least one slot 3 on surface 4 and the block 2 comprises a notch 5. As illustrated in FIG. 1, the notch 5 comprises a "V" ("Chevron") notch 5 on an opposite surface 6, and having its apex 13 substantially co-linear with the slot 3. This configuration of a notch 5 is merely exemplary of notches within the scope of the invention. The scope of the invention comprises notches of varying sizes, shapes, and configurations, for example and in no way limiting of the invention, rectangular, curved; and combinations thereof.

The slot 3 comprises a thickness "t", for example a constant thickness "t" in a range from about 10 micrometers ($\mu$m) to about 1 millimeter (mm), and a length in a range from about 1 mm to about 10 mm. The slot 3 and "V" notch 5 are formed in the block 2 by an appropriate process, such as, but not limited to, a wire electro-discharge machining (WEDM) process, in step S1 (FIG. 3).

The depth of the "V" notch 5 is generally similar to the depth of the slot 3. The "V" notch 5 and slot 3 define a bridge 7 of solid material in the block 2 that is disposed between the slot 3 and "V" notch 5. Typically, the height H, width W, thickness T of the standard are in a range from about 0.5 centimeter to about 10.0 centimeters. For example, the ratio H/T is in a range from about 0.5 to about 2.0, and the ratio of W/H is in a range from about 0.5 to about 1.0.

After the "V" notch 5 and the slot 3 are formed in the standard 1, the block 2 is cleaned in step S2 to remove any residue from the slot-structure formation processes. For example, if a machining process is used to form the slot structure, the block is cleaned to remove residue, such as but not limited to, oils, machining chips, recast and oxide deposits, and the like.

If the slot 3 is formed with a thickness t that simulates a relevant defect thickness, no compression is needed. If the thickness "t" of the slot 3 is greater than the thickness desired for use as a standard, the slot 3 can be compressed to a more desired final thickness. The block 2 is compressed (step S3) by applying a distributed force on surfaces 18 and 19 in a direction indicated by arrows 10 (FIG. 1). The formation of a slot structure, including any compression of the slot(s) creates a structure that simulates a defect, where defect includes cracks, holes, crevices, and other hard-to-reach surfaces (hereinafter "simulated defect").

After the optional compression, the block 2 is exposed to a thermal treatment in step S4. An exemplary thermal treatment, which is within the scope of the invention, comprises, but is not limited to, a solution heat treatment followed by controlled exposure to a high-temperature, oxidizing environment for a time period sufficient to form oxides on both the block surface and the inside of the simulated defect.

The standard 1, with the oxide-filled simulated defect can be used for oxide-removal process evaluation. The evaluation comprises disposing the oxidized standard 1 in a cleaning reactor. The scope of the invention comprises any cleaning reactor and any oxide removal process that the reactor can employ. The exact type of cleaning reactor and process used does not affect the standard per se. The standard 1 is placed, by itself, and alternatively with other standards, in a reactor. Alternatively, the standard 1 is placed in the reactor with turbine components to be cleaned. The standard 1 is then subjected to an oxide removal process, in step S5. Once the oxide removal process is complete, the standard 1 is removed from the reactor for evaluation.

The evaluation of the standard 1 comprises exposing the simulated defect and its surfaces in step S6. The simulated defect is exposed by compressing the standard 1 at the "V" notch 5, in the direction of arrows 11 (FIG. 1), thus splitting the standard 1 to open the simulated defect.

Evaluation of the simulated defect, in step S7, can also include metallographically sectioning the standard 1. The surfaces of the exposed slot 3 are evaluated for extent of oxide removal using various, known evaluation techniques. These evaluation techniques, include, but are not limited to, optical inspection, electrical resistivity measurement, weight loss measurement, and wetability evaluation.

Figure 3:
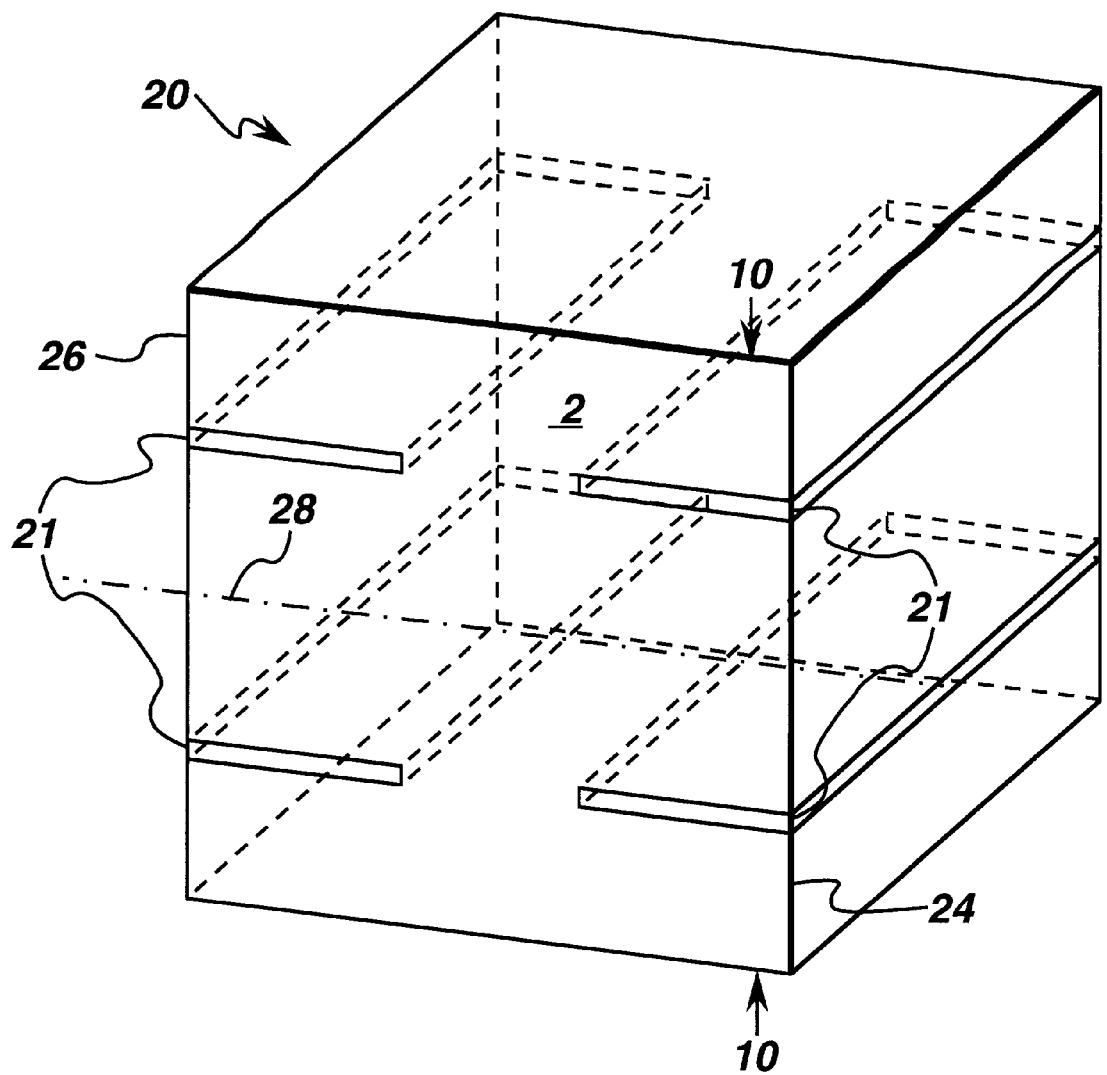
FIG. 3 is a schematic illustration of a second standard for evaluating effectiveness of oxide removal processes.

A second embodiment of a standard 20, as embodied by the invention, is illustrated in FIG. 3, and its formation and use are similar to that described above with respect to FIG. 2. The standard 20 comprises a block 2 of solid material. The simulated defect for the standard 20 comprises at least one slot 21, which is formed similar to slot 3 described above. For example, the slot structure comprises multiple slots 21, which are machined into the block 2, for example at least one slot in each of surfaces 24 and 26. The following description discusses multiple slots 21, however this is merely exemplary of the invention and is not meant to limit the invention in any way.

The standard 20 is cleaned (step S2) and, if desired, compressed (step S3) as described above to form simulated defects. The standard 20 is then subjected to a heat treatment to oxidize the surface and slot structure. The standard 20 is then oxidized (step S4), as discussed above. The standard 20 is then disposed in a cleaning reactor, and subjected to an oxide removal operation (step S5).

Once the oxide removal operation is complete, the standard, which comprises the simulated defect slot structure, is ready for evaluation. The evaluation comprises exposing the crack-like defect, such as by metallographic sectioning, in step S6 and evaluating in step S7.

The standards 1 and 20 are evaluated for oxide removal, based on the known starting defect. The evaluation of oxide removal provides an indication of the effectiveness of the oxide removal capabilities of the oxide removal process. For example, and in no way limiting of the invention, performing an oxide removal process for a prescribed time on a standard having known oxide amount and in a reactor with known operational specifications provides oxide removal process benchmarks, which are indicative of the oxide removal process performance.

The standard can be used as an oxide-removal process guage to determine oxide removal process progress. The standard indicates the degree of oxide removal. For use as an oxide-removal process gauge, a standard is prepared with known oxide amounts. The standard is placed in a reactor and cleaned, as discussed above. The standard, which is disposed in the reactor, can be checked for the degree of oxide removal against the oxide removal process benchmarks. Therefore, it is possible to gauge whether a oxide removal process has removed sufficient oxide amounts for turbine components.

Either of the standard structures described above can be used to evaluate braze or welding repair effectiveness. In a braze-repair effectiveness evaluation process, a simulated defect structure is provided in a standard, the standard is oxidized, and then cleaned, as described above in steps Si through S5. A braze alloy is disposed on at least some portion of the standard and may be placed over at least one of the simulated defect structures. The standard then undergoes brazing and, if necessary, any subsequent thermal treatments, as known in the art, to form a brazed standard. The brazed standard is evaluated, as discussed above in step S7. For example, the brazed standard is metallographically sectioned, inspected, and evaluated for braze-repair parameters. Exemplary braze repair parameters comprise, but are not limited to, extent of oxide removal, depth of braze filling, and alloying element depletion. The evaluation of the brazed standard provides an indication of the effectiveness of the brazing preparation steps and the effectiveness of the braze repair process.

As discussed above, the standard's simulated defect structure configuration may vary. While the above description sets forth an elongated and planar slot, this slot configuration is merely exemplary of slot configurations within the scope of the invention. For example, the scope of the invention comprises a simulated defect that simulates cooling hole dimensions, which is used to determine oxide removal from cooling holes in a turbine component.

The standards, as embodied by the invention, are also useful as tools for determining desirable operational bounds for oxide-removal processes. As known in the art, oxide removal depends on various factors, including but not limited to, oxide-removal process temperature, process atmosphere, and process time. As an exemplary use as a process improvement tool, standards are formed of the same base material with similarly structured slots as a turbine component of interest. The nature and extent of oxidation is essentially identical between the standards. A standard is subjected to an oxide cleaning run under a first set of process conditions. A second run using a second standard is made varying at least one process condition. Subsequent runs using other standards vary other process conditions. Oxide removal amounts and other parameters for each of the runs are determined. An enhanced combination of oxide-removal process conditions, for example an enhanced oxide-removal amount.

An exemplary method of forming a standard will now be discussed. This method is merely exemplary and not meant to limit the invention in any way. A first step in the preparation of a standard involves using a wire electro-discharge machine (WEDM) to form slots in the standard. The structure and operation of standard WEDMs are known by those of ordinary skill in the art, and thus a detailed description is not provided. The standard is then etched and degreased to remove a recast layer therefrom.

The standard is then compressed, if needed. The compression occurs in a press that comprises tungsten carbide platens. The standard is oriented in the press to apply a force in the direction of arrows 10 (FIGS. 1 and 3). The standard is compressed with a suitable force to form crack-like defects. When the applied force is removed, and the slot reopens slightly due to elastic unloading of the material. The standard's slots are now reduced in thickness t to less that about 50% of the original thickness. For example, if 0.10 mm wire is used to make a simulated defect in the form of a slot having a thickness of about 0.12 mm, the simulated defect slot defect may be compressed to less than about 0.05 mm.

The solution heat treatment of the standard comprises placing the standards on an alumina tray, so the slot structures are out of contact with the tray and adjacent standards do not touch. The tray is then placed into an air furnace. The temperature in the furnace is increased to about 1250° C. at a rate of about 25° C./min and held for about 1 hour to solution the material. The standards are next oxidized at a temperature of about 1150° C. for about 300 hours. Thereafter, the furnace is cooled to a temperature below about 100° C. at a rate sufficient to form dense oxides in the simulated defects.

While various embodiments are described herein, it will be appreciated from the specification that various combinations of elements, variations or improvements therein may be made by those skilled in the art, and are within the scope of the invention.

We claim:

1. A tool for determining oxide removal parameters of an oxide removal process, the tool comprising:

a block of material, the block being formed of a material upon which an oxide can be formed, wherein said block comprises
at least one oxide-filled slot disposed in a first face of the block of material; and
a notch disposed in a second face of the block, said second face opposite to said first face, said notch disposed to be co-linear with the slot to form a material bridge between the notch and the slot;
wherein said slot has a structure that simulates a defect in a metal article, and wherein the oxide removal parameters comprise at least one of:
extent of oxide removal from the slot and the surfaces of the generally rectangular solid block of material, braze repair capability, depth of braze filling, and alloying element depletion at the slot and surfaces of the block of material.

2. A tool according to claim 1, wherein the block of material comprises a nickel-, cobalt-, or iron-nickel-based superalloys, or combinations thereof.

3. A tool according to claim 1, wherein the block of material comprises a generally rectangular solid block of material.

4. A tool according to claim 1, wherein the at least one slot comprises a constant thickness in a range from about 10 micrometers ($\mu$m) to about 1 millimeter (mm) and a depth in a range from about 10 micrometers to about 10 millimeters.

5. A tool according to claim 1, wherein the notch comprises a "V" notch in the block of material.

6. A tool according to claim 1, wherein the oxide removal process parameters are determined by an evaluation comprising at least one of:

optical inspection, brazing evaluation, weight loss measurement, electrical resistivity measurement, and wetability evaluation.

* * * * *